(12) United States Patent
Melanson et al.

(10) Patent No.: US 9,880,166 B2
(45) Date of Patent: Jan. 30, 2018

(54) SENSITIVE AND RAPID METHOD FOR DETECTION OF LOW LEVELS OF LAL-REACTIVE SUBSTANCES

(71) Applicant: General Electric Company, Schenectady, NY (US)

(72) Inventors: Paul Charles Melanson, Boulder, CO (US); Vidyasankar Sundaresan, Trevose, PA (US); Richard Douglas Godec, Boulder, CO (US); Shouquan Deng, Shanghai (CN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/434,364

(22) PCT Filed: Oct. 7, 2013

(86) PCT No.: PCT/US2013/063645
§ 371 (c)(1),
(2) Date: Apr. 8, 2015

(87) PCT Pub. No.: WO2014/058758
PCT Pub. Date: Apr. 17, 2014

(65) Prior Publication Data
US 2015/0233917 A1      Aug. 20, 2015

Related U.S. Application Data

(60) Provisional application No. 61/710,898, filed on Oct. 8, 2012, provisional application No. 61/710,908, filed (Continued)

(51) Int. Cl.
*C12Q 1/00* (2006.01)
*C12Q 1/68* (2006.01)
(Continued)

(52) U.S. Cl.
CPC ....... *G01N 33/56911* (2013.01); *G01N 21/17* (2013.01)

(58) Field of Classification Search
CPC ...... G01N 1/40; G01N 30/6091; G01N 30/88; G01N 31/00; G01N 33/56911;
(Continued)

(56) References Cited

U.S. PATENT DOCUMENTS 3,971,186 A   7/1976   Havelka et al.
4,717,658 A   1/1988   Michaels
(Continued)

FOREIGN PATENT DOCUMENTS

CA   2156226 A1   2/1996
CA   2420682 A1   3/2002
(Continued)

OTHER PUBLICATIONS

Lonza, (Limulus Amebocyte Lysate, Kinetic—QCLTM, Jan. 2011—p. 1-19).*
(Continued)

*Primary Examiner* — Jana A Hines
(74) *Attorney, Agent, or Firm* — Wegman, Hessler & Vanderburg

(57) ABSTRACT

Methods and systems for measuring the concentration of LAL-reactive substances in fluid samples is provided. They include contacting an aqueous sample with a detection reagent to form a prepared sample. A physical property of the prepared sample may be measured to obtain at least one sample measurement characteristic of the prepared sample. Curve fitting may then be used to forecast a concentration of the LAL-reactive substance the aqueous sample will have at a specified time in the future based on the sample measurement and a correlation developed between at least one standard measurement of a physical quality of a solution
(Continued)

with a known concentration of a LAL-reactive substance therein. The quality of the sample measurement may be validated using historical data and/or the standard measurement.

16 Claims, 3 Drawing Sheets

Related U.S. Application Data on Oct. 8, 2012, provisional application No. 61/710,990, filed on Oct. 8, 2012, provisional application No. 61/710,903, filed on Oct. 8, 2012.

(51) Int. Cl.
  *G01N 33/53* (2006.01)
  *G01N 33/569* (2006.01)
  *G01N 21/17* (2006.01)

(58) Field of Classification Search
  CPC ............ G01N 33/579; G01N 2400/50; G01N 2400/10; B01L 3/00
  USPC .................... 435/4, 6.15; 436/8, 807, 808
  See application file for complete search history.

(56) References Cited

U.S. PATENT DOCUMENTS

| | | | |
|---|---|---|---|
| 4,819,713 A | 4/1989 | Weisman | |
| 4,824,303 A | 4/1989 | Dinger | |
| 4,879,634 A | 11/1989 | Storrow et al. | |
| 4,909,752 A | 3/1990 | Hallum et al. | |
| 5,010,444 A | 4/1991 | Storrow et al. | |
| 5,071,013 A | 12/1991 | Peterson | |
| 5,220,485 A | 6/1993 | Chakrabarti | |
| 5,224,016 A | 6/1993 | Weisman et al. | |
| 5,550,030 A | 8/1996 | Tanaka et al. | |
| 5,571,683 A | 11/1996 | Nakajima et al. | |
| 5,726,404 A | 3/1998 | Brody | |
| 5,859,764 A | 1/1999 | Davis et al. | |
| 6,212,075 B1 | 4/2001 | Habing et al. | |
| 6,270,982 B1 | 8/2001 | Jordan et al. | |
| 6,285,564 B1 | 9/2001 | O'Brien | |
| 6,687,130 B2 | 2/2004 | Adams, Sr. et al. | |
| 6,900,019 B1 | 5/2005 | Horton | |
| 7,031,167 B1 | 4/2006 | Zagoory et al. | |
| 7,180,737 B2 | 2/2007 | Straub, Jr. et al. | |
| 7,322,843 B1 | 1/2008 | Lee et al. | |
| 7,349,221 B2 | 3/2008 | Yurko | |
| 7,807,448 B2 | 10/2010 | Glezer et al. | |
| 8,045,332 B2 | 10/2011 | Lee et al. | |
| 2002/0137218 A1 | 9/2002 | Mian et al. | |
| 2002/0185183 A1 | 12/2002 | O'Connor et al. | |
| 2004/0121450 A1 | 6/2004 | Pugia et al. | |
| 2004/0131450 A1 | 7/2004 | Yang | |
| 2005/0026239 A1 | 2/2005 | Castro et al. | |
| 2005/0048655 A1 | 3/2005 | Novitsky et al. | |
| 2005/0106066 A1 | 5/2005 | Saltsman et al. | |
| 2005/0170515 A1 | 8/2005 | Moore | |
| 2007/0231217 A1 | 10/2007 | Clinton et al. | |
| 2007/0253169 A1 | 11/2007 | Clawser | |
| 2008/0187445 A1 | 8/2008 | Gale et al. | |
| 2008/0190220 A1 | 8/2008 | Backes et al. | |
| 2008/0239690 A1 | 10/2008 | Harvey et al. | |
| 2009/0139578 A1 | 6/2009 | Kim et al. | |
| 2009/0311796 A1 | 12/2009 | Griss et al. | |
| 2010/0330597 A1 | 12/2010 | Tsuchiya | |
| 2011/0079094 A1 | 4/2011 | Gransee et al. | |
| 2011/0124132 A1 | 5/2011 | Kim et al. | |
| 2011/0143364 A1 | 6/2011 | Kim et al. | |
| 2011/0201049 A1 | 8/2011 | Wainwright et al. | |
| 2011/0261537 A1 | 10/2011 | Sporer et al. | |
| 2012/0244607 A1 | 9/2012 | Iwamoto et al. | |
| 2015/0060272 A1 | 3/2015 | Blidner et al. | |

FOREIGN PATENT DOCUMENTS

| | | | |
|---|---|---|---|
| CA | 2820483 A1 | 7/2007 | |
| CA | 2732011 A1 | 2/2010 | |
| CA | 2755276 A1 | 9/2010 | |
| CN | 1208464 A | 2/1999 | |
| CN | 101368967 A | 2/2009 | |
| CN | 101387647 A | 3/2009 | |
| CN | 101389960 A | 3/2009 | |
| CN | 101529246 A | 9/2009 | |
| CN | 102177439 A | 9/2011 | |
| CN | 102441356 A | 5/2012 | |
| EP | 0320154 A1 | 6/1989 | |
| EP | 0649021 A1 | 4/1995 | |
| EP | 0690308 A2 | 1/1996 | |
| EP | 0921397 A1 | 6/1999 | |
| EP | 0957366 A1 | 11/1999 | |
| EP | 1983347 A2 | 10/2008 | |
| JP | 6193958 A | 5/1986 | |
| JP | 10253630 A | 9/1998 | |
| JP | 2001503854 A | 3/2001 | |
| JP | 2003533681 A | 11/2003 | |
| JP | 2004212120 A | 7/2004 | |
| JP | 2005519304 A | 6/2005 | |
| JP | 2007501020 A | 1/2007 | |
| JP | 2010042020 A | 2/2010 | |
| WO | 9721090 A1 | 6/1997 | |
| WO | 199943432 A1 | 9/1999 | |
| WO | 2004065930 A2 | 8/2004 | |
| WO | 2006009724 A2 | 1/2006 | |
| WO | 2006069757 A1 | 7/2006 | |
| WO | 2006070376 A1 | 7/2006 | |
| WO | WO 2007/052648 A1 | 10/2007 | |
| WO | 2009005231 A1 | 1/2009 | |
| WO | 2009105711 A1 | 8/2009 | |
| WO | 2011096782 A2 | 8/2011 | |

OTHER PUBLICATIONS

WinKQCL® 4: Endotoxin Detection and Analysis Software. Lonza. Copyright Mar. 2009).*
Nichols et al., (LALReview. PryoSense®—PAT for WFI. Published by Lonza. 2008 Issue 1: pp. 1-6).*
Paul Charles Melanson et al., filed Apr. 8, 2015, U.S. Appl. No. 14/434,312.
Richard Douglas Godec et al., filed Apr. 8, 2015, U.S. Appl. No. 14/434,361.
Richard Douglas Godec et al., filed Apr. 8, 2015, U.S. Appl. No. 14/434,273.
The United States Pharmacopeia, "Bacterial Endotoxins Test", Biological Tests and Assays, USP Chapter 85, Reissue, pp. R65-R69, Oct. 1, 2010.
European Pharmacopoeia, "2.6.14 Bacterial Endotoxins", Seventh Edition, Volume No. 1, pp. 171-175, 2010.
American National Standard, "Bacterial Endotoxins-Test Methods, Routine Monitoring, and Alternatives to Batch Testing", ANSI/AAMI ST72:2011, pp. 1-34, 2011.
The Japanese Pharmacopeia, "4.01 Bacterial Endotoxin Test", Sixteenth Edition, pp. 92-96, 2011.
Harwood, "3-Dimensional Compact Disc (CD) Microfluidic Platform", A Thesis, pp. 1-78, 2011.
ICH Harmonised Tripartite Guideline, "Evaluation and Recommendation of Pharmacopoeial Texts for Use in the ICH Regions on Bacterial Endotoxins Test General Chapter", Q4B Annex 14, Step 4 version, Oct. 18, 2012.
The United States Pharmacopeia, "Transfusion and Infusion Assemblies and Similar Medical Devices", USP Chapter 161, vol. No. 1, pp. 131-131, May 1, 2013.
PCT Search Report and Written Opinion issued in connection with related Application No. PCT/US2013/63639 on Jun. 25, 2014.
Unofficial English Translation of Chinese Office Action issued in connection with related CN Application No. 201380052528.7 on Oct. 27, 2015.
Baines, "Endotoxin Testing" In: Handbook of Microbiological Quality Control in Pharmaceuticals and Medical Devices, pp. 144-167, 2003.

(56) References Cited

OTHER PUBLICATIONS

"Endotoxin Detection: Products and Services", Lonza, pp. 1-36, May 1, 2010.
Unofficial English Translation of Chinese Office Action issued in connection with related CN Application No. 201380052524.9 on Dec. 4, 2015.
Hemker et al., "The Kinetics of Enzyme Cascade Systems," Proceedings of the Royal Society of London, B (Biological Sciences), Volume No. 173, pp. 411-420, 1969.
Bryant et al., "Endotoxin Contamination of Enzyme Conjugates Used in Enzyme-Linked Immunosorbent Assays", Journal of Clinical Microbiology, Volume No. 17, Issue No. 6, pp. 1050-1053, Jun. 1983.
Chang et al., "Feasibility of on-chip detection of endotoxin by LAL test", Biotechnology and bioprocess engineering, pp. 132-136, Jan. 1, 2004.
Gee et al., "A Multi-Center Comparison Study between the Endosafe PTS(TM) Rapid Release Testing System and Traditional Test Methods for Detecting Endotoxin in Cell Therapy Products", Volume No. 10, Issue No. 4, pp. 427-435, Aug. 22, 2008, from "Cytotherapy, Author Manuscript".
Mitsumoto et al., "Novel endotoxin assay by laser light-scattering particle-counting method", Journal of Clinical Laboratory Analysis, Volume No. 23, Issue No. 2, pp. 117-124, Jan. 1, 2009.
Tsougeni et al., ""Smart" Polymeric Microfluidics Fabricated by Plasma Processing: Controlled Wetting, Capillary Filling and Hydrophobic Valving", Lab chip, Volume No. 10, pp. 462-469, Nov. 30, 2009.
Cooper et al., "Automated endotoxin testing program for high-risk-level compounded sterile preparations at an institutional compounding pharmacy", American Journal of Health-System Pharmacy: AJHP : Official Journal of The American Society of Health-System Pharmacists, Volume No. 67, Issue No. 4, pp. 280-286, Feb. 15, 2010.
"Limulus Amebocyte Lysate (LAL1) Kinetic-QCL(TM)", Lonza, pp. 1-19, Jan. 1, 2011.
International Search Report and Written Opinion issued in connection with corresponding PCT Application No. PCT/US2013/038638 dated Jan. 7, 2014.
International Search Report and Written Opinion issued in connection with corresponding PCT Application No. PCT/US2013/063625 dated Jan. 24, 2014.
International Search Report and Written Opinion issued in connection with corresponding PCT Application No. PCT/US2013/063645 dated Feb. 17, 2014.
International Invitation to Pay Additional Fees issued in connection with corresponding PCT Application No. PCT/US2013/063649 dated Feb. 17, 2014.
International Search Report and Written Opinion issued in connection with corresponding PCT Application No. PCT/US2013/063649 dated Apr. 30, 2014.
US Non-Final Office Action issued in connection with Related U.S. Appl. No. 14/434,361 dated Oct. 26, 2016.
Unofficial English Translation of Chinese Office Action issued in connection with related CN Application No. 201380052528.7 dated Jul. 12, 2016.
Office Action dated Sep. 8, 2017 in related U.S. Appl. No. 14/434,312.
English Translation of Notification for Reasons for Refusal from JPO issued in Japanese Application No. 2015-535859 dated Jul. 10, 2017.
English Translation of Notification for Reasons for Refusal from JPO issued in Japanese Application No. 2015-535855 dated Jul. 13, 2017.

* cited by examiner

SENSITIVE AND RAPID METHOD FOR DETECTION OF LOW LEVELS OF LAL-REACTIVE SUBSTANCES

CROSS-REFERENCE TO RELATED APPLICATIONS

This is a national stage application under 35 U.S.C. § 371(c) of prior-filed, co-pending, PCT application serial number PCT/US2013/063645, filed on Oct. 7, 2013, which claims priority to Provisional Patent Application Ser. No. 61/710,908 filed Oct. 8, 2012 and titled MICROFLUIDIC BACTERIA ENDOTOXIN TESTING METHOD AND APPARATUS; Provisional Patent Application Ser. No. 61/710,990 filed Oct. 8, 2012 and titled CENTRIPETAL MICROFLUIDIC PLATFORM FOR BACTERIAL ENDOTOXIN TESTING; Provisional Patent Application Ser. No. 61/710,898 filed Oct. 8, 2012 and titled SENSITIVE AND RAPID METHOD FOR DETECTION OF LOW LEVELS OF ENDOTOXINS USING LAL REAGENTS; and Provisional Patent Application Ser. No. 61/710,903 filed Oct. 8, 2012 and titled MICROPLATES PRELOADED WITH ENDOTOXIN DETECTION REAGENTS WITH CALIBRATION MEANS. All of the above listed applications are herein incorporated by reference.

FIELD OF THE INVENTION

Embodiments of the invention relate to the field of determining the concentration of LAL-reactive substances in an aqueous sample. More specifically, embodiments of the invention relate to LAL-reactive substances measurement methods and systems.

BACKGROUND OF THE INVENTION

Microbial contamination, such as Gram positive bacteria, Gram negative bacteria, yeast, and fungi may cause severe illness and even death in humans. When people become infected with gram negative bacteria, the bacteria may produce fever-inducing bacterial endotoxins or endotoxin molecules. Endotoxin molecules may be a source of contamination even when no microbes are present. Endotoxin molecules can be dangerous, lead to toxic shock, or even be deadly to humans.

Manufacturers in certain industries, especially the pharmaceutical, medical device and food industries, must meet certain standards to make sure their products do not contain microbial or endotoxin contamination. These industries require frequent, accurate, and sensitive testing for the existence of endotoxins to meet various safety standards, such as those set by the United States Food and Drug Administration, or the Environmental Protection Agency.

Currently, a variety of assays have been developed to detect the presence of endotoxin in or on the sample being tested using hemocyte lysates from horseshoe crabs. Clotting will occur when the hemocyte lysate is exposed to the endotoxin. Hemocyte lysate is amoebocyte lysate produced from the hemolymph of various horseshoe crab species, including the *Limulus, Tachypleus,* and *Carcinoscorpius* species. A commonly used amoebocyte lysate, produced from the hemolymph of the *Limulus* species, is referred to as *Limulus* amoebocyte lysate ("LAL").

Routine assays that use LAL include, gel clot assays, end point turbidimetric assays, kinetic turbidimetric assays, endpoint chromogenic assays, and kinetic chromogenic assays. More information on these assays and the standards used may be found in United States Pharmacopeia ("USP") Chapter 85 "Bacterial Endotoxins Test" ("BET"), Japanese Pharmacopeia 4.01 "Bacterial Endotoxin Test", European Pharmacopoeia Feb. 6, 2014 "Bacterial Endotoxins", and other equivalent national Pharmacopeias. Additional internationally harmonized pharmacopeia information can be found in ICH Q4B Annex 14 "Bacterial Endotoxin Test General Chapter". For endotoxin testing in medical devices, information can be found in USP Chapter 161 "Transfusion and Infusion Assemblies and Similar Medical Devices" and ANSI/AAMI ST72 "Bacterial endotoxins—Test methods, routine monitoring, and alternatives to batch testing".

Typical chromogenic and turbidometric BET assays are run in well plates, with measurements of absorbance being conducted by plate readers designed to run 24, 96 and 384 well plates. In all these cases, the kinetic assay requires measurement of time required to reach a specified onset optical density (absorbance). Therefore, absorbance values are measured at periodic intervals for all samples and standards being tested in a single plate. As the reaction progresses, the optical density ("OD") increases with time, but it is impossible to expect that an actual measurement be equal to the exact specified onset optical density. Data analysis is required for data on consecutive measurements, in order to calculate the time at which the optical density of the sample reached and passed the specified onset value. Such analysis typically involves either a simple linear interpolation between two consecutive time-stamped data points with measured values less than and greater than the specified onset value, or linear or non-linear curve fitting over a larger set of data points in the neighborhood of the specified onset value. The time required to reach onset OD is inversely correlated with endotoxin concentrations, so that testing for low levels of endotoxin necessarily requires longer assay times. This is typically an hour or more for measuring 0.005 EU/mL distinguished from a blank (negative control), depending on the manufacturer and type of the LAL reagent.

Turbidimetric assays usually require longer times than the chromogenic assays using comparable LAL reagent in conjunction with a chromophoric substrate. The chromogenic assays, which incorporate a chromogenic substrate with an absorbance peak at 405 nm, may be performed either in an endpoint mode or in a kinetic mode. In chromogenic assays, the time dependence of the optical density measured at 405 nm shows a substantial initial period during which the OD remains close to zero, often called "initial lag time". The initial lag time is followed by a period in which OD starts to rise, or "initial slope". The initial lag time becomes shorter as the endotoxin concentration increases, while the initial slope of the OD response increases with endotoxin concentration. The endpoint mode correlates endotoxin levels with the OD at 405 nm achieved at a specified time. The kinetic mode correlates endotoxin levels with the time required to achieve a specified onset OD at 405 nm, typically defined as OD=0.2. Both the endpoint assay and kinetic assay have long run times, typically greater than 60 minutes, in order to get the resolution between a blank control and desired lower detection limits of 0.005 EU/mL or 0.001 EU/mL.

In cases where assay results need to be obtained quickly, it is therefore desirable to have methods of data analysis that correlate reliably with endotoxin concentration at earlier times in the assay. As such, several methods have been developed to estimate endotoxin concentration at earlier times in the assay.

One method is a dynamic light scattering method that obtains results from a turbidimetric assay quicker than the currently performed static light scattering method. Another method uses an apparatus that uses light scattering measurements for turbidimetric assay in conjunction with a time function difference method and a multi-series difference method to correlate assay times with endotoxin concentration. Another method uses a correlation of endotoxin concentration with initial rate of increase in scattered light detected in a turbidimetric assay. Although all these methods may reduce the time required to obtain the endotoxin concentration of a given sample, they all rely on correlation or linear methods of forecasting. Nor do these methods allow the user to correlate the data to compendia requirements or standards. Moreover, none of these methods are capable of alerting the user to anomalies in the measurement.

BRIEF DESCRIPTION OF THE INVENTION

It was surprisingly discovered that monitoring the reaction kinetics of the LAL and endotoxin reaction allows the user to validate or assess whether there is an anomaly in the sample analysis in addition to predicting the concentration of any endotoxin that may be present in the sample. Some OD responses, such as lag time, initial slope, the rate of change of slope of absorbance over time, and the maximum slope of measured absorbance against time, etc., correlate well with endotoxin concentrations in a given sample. Additionally, for kinetic assays, where the time required to reach a threshold absorbance is correlated with endotoxin concentration, it was surprisingly discovered that prediction of the onset time is possible in a dynamic basis as absorbance data are collected. This allows the endotoxin concentration to be calculated earlier than the actual time required to reach the specified absorbance threshold. The strategy used for such prediction is dependent upon the concentration range of the endotoxin standards used for calibration. Accordingly methods are disclosed that are sensitive and fast, even at low endotoxin concentrations. The methods may be used with any photometric method, including turbidimetric and chromogenic methods.

In one embodiment, a method for measuring the concentration of a LAL-reactive substance in an aqueous sample is disclosed. The method may comprise contacting an aqueous sample with a detection reagent to form a prepared sample. A physical property of the prepared sample may be measured to obtain at least one sample measurement characteristic of the prepared sample. Curve fitting may then be used to forecast a concentration of the LAL-reactive substance the aqueous sample will have at a specified time in the future based on the sample measurement and a correlation developed between at least one standard measurement of a physical property of a solution with a known concentration of a LAL-reactive substance therein. The quality of the sample measurement may be validated using historical data and/or the standard measurement.

In another embodiment, the physical property may be an optical property. Suitable optical properties include, but are not limited to, transmittance, absorbance, turbidity, light scattering, optical density, color, color value, hue, spectrum, chemiluminescence, fluorescence, magnetic resonance of absorbance over time, time to a fixed change in absorbance, maximum slope of absorbance over time, and absorbance after a fixed time.

In yet another embodiment, the physical property may be a non-linear property such as reaction kinetics. The quality of the sample measurement may be validated using the non-linear property. Types of reaction kinetics include, but are not limited to, an endotoxin reaction, a glucan reaction, and a combination thereof. In another embodiment, the method may further comprise including at least one apparent time delay of the cascade initiation of the reaction as a variable in the curve fitting step.

In another embodiment of the invention, a method for measuring concentration of a LAL-reactive substance in an aqueous sample is disclosed comprising contacting the aqueous sample with a detection reagent to form a prepared sample. A physical property of the prepared sample may be measured to obtain at least two sample measurements characteristic of the prepared sample. A concentration of the LAL-reactive substance the aqueous sample will have at a specified time in the future may be forecasted. The forecasted concentration may be based on the sample measurements and a correlation developed between the non-linear behavior of at least three standard measurements of a physical property of a solution with a known concentration of a LAL-reactive substance therein.

In another embodiment, the physical property may be an optical property. Suitable optical properties include, but are not limited to, transmittance, absorbance, turbidity, light scattering, optical density, color, color value, hue, spectrum, chemiluminescence, fluorescence, magnetic resonance of absorbance over time, time to a fixed change in absorbance, maximum slope of absorbance over time, and absorbance after a fixed time.

In yet another embodiment, the physical property may be a non-linear property based on known reaction kinetics of the reaction between the detection reagent and LAL-reactive substance. Suitable reactions include, but are not limited to, an endotoxin reaction, a glucan reaction, and a combination thereof.

In another embodiment of the invention, a system for measuring a concentration of a LAL-reactive substance in an aqueous sample is disclosed. The system may comprise a memory and a processor operatively connected with the memory. The processor may be programmed to receive at least one input comprising a sample measurement. The sample measurement may be a measured physical property characteristic of the aqueous sample. The processor may also be programmed to use curve-fitting to generate at least one output. The output may comprise a forecasted concentration of the LAL-reactive substance the aqueous sample will have at a specified time in the future based on the sample measurement and a correlation. The correlation may be developed between at least one standard measurement of a physical property of a solution with a known concentration of a LAL-reactive substance therein. The outputs may also comprise a validated sample measurement wherein the quality of the sample measurement was validated. The quality may be validated using historical data and/or the standard measurements. The processor may also be programmed to report and/or store the output in the memory. In yet another embodiment, the system may further comprise an optical reader operatively connected to the processor.

In another embodiment of the system the physical property may be an optical property. Suitable optical properties include, but are not limited to, transmittance, absorbance, turbidity, light scattering, optical density, color, color value, hue, spectrum, chemiluminescence, fluorescence, magnetic resonance of absorbance over time, time to a fixed change in absorbance, maximum slope of absorbance over time, and absorbance after a fixed time.

In yet another embodiment, the physical property may be a non-linear property, such as reaction kinetics. Suitable reactions include, but are not limited to, an endotoxin reaction, a glucan reaction, and a combination thereof. In another embodiment, the processor may be further programmed to include at least one apparent time delay of the cascade initiation of the reaction as a variable in the curve fitting step.

In another embodiment of the invention, a system for measuring a concentration of a LAL-reactive substance in an aqueous sample is disclosed. The system may comprise a memory; and a processor operatively connected with the memory. The processor may be programmed to receive at least one input. The input may comprise at least two sample measurements, wherein the sample measurements are a measured physical property characteristic of the aqueous sample. The processor may use a correlation developed between the non-linear behavior of at least three standard measurements of a physical property of a solution with a known concentration of a LAL-reactive substance therein to generate at least one output. The output may comprise a forecasted concentration of the LAL-reactive substance the aqueous sample may have at a specified time in the future. The processor may also be programmed to report and/or store the output in the memory. In yet another embodiment, the system may further comprise an optical reader operatively connected to the processor.

In another embodiment, the physical property may be an optical property. Suitable optical properties include, but are not limited to, transmittance, absorbance, turbidity, light scattering, optical density, color, color value, hue, spectrum, chemiluminescence, fluorescence, magnetic resonance of absorbance over time, time to a fixed change in absorbance, maximum slope of absorbance over time, and absorbance after a fixed time.

In yet another embodiment, the physical property may be a non-linear property. The non-linear property may be based on known reaction kinetics of the reaction between the detection reagent and LAL-reactive substance. Suitable reactions include, but are not limited to, an endotoxin reaction, a glucan reaction, and a combination thereof.

DETAILED DESCRIPTION OF EXEMPLARY EMBODIMENTS

Figure 1:
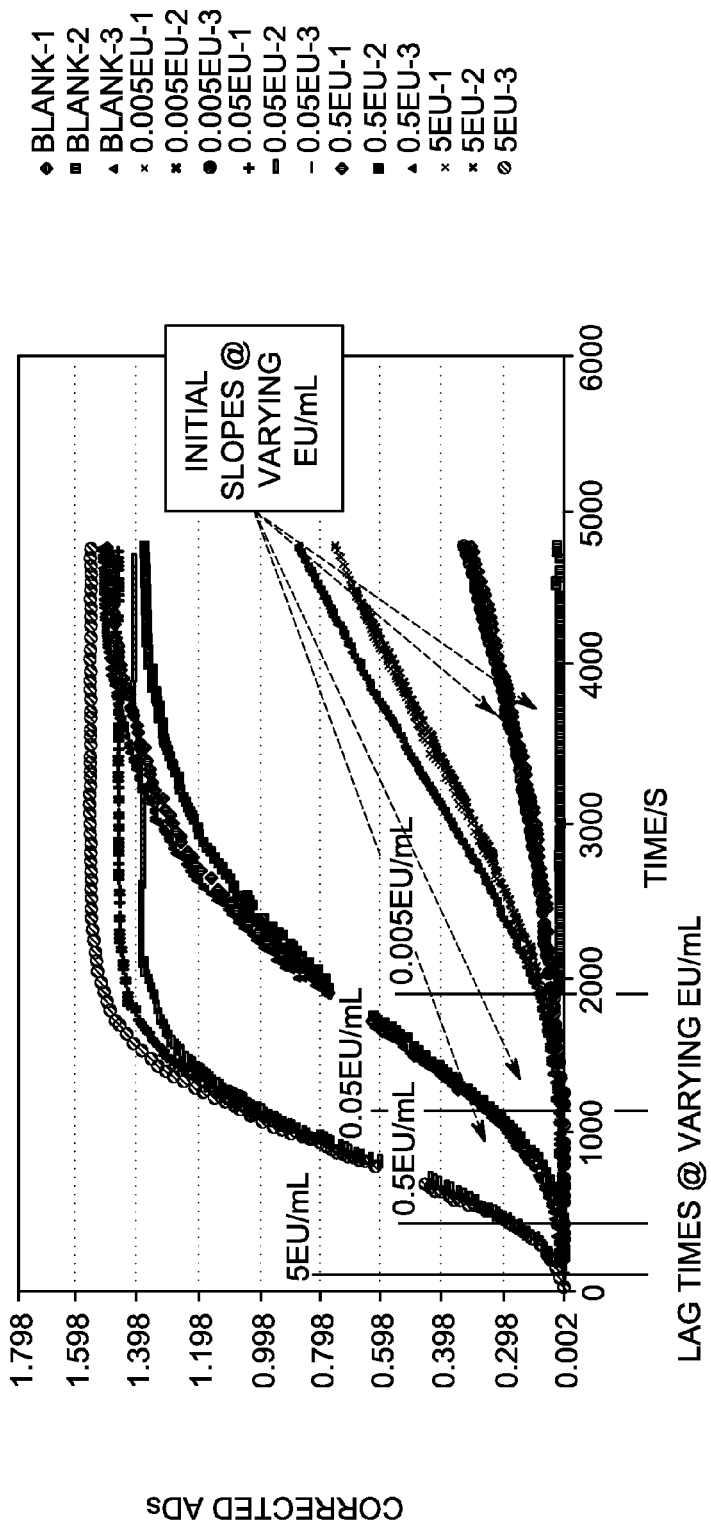
FIG. 1 shows an embodiment of the invention wherein the initial lag times and initial slopes at various endotoxin concentrations are marked.

Several frequently used terms in the specification may be defined as follows. The following definitions are intended to aid in understanding the invention are not intended to limit the invention to the terms as used herein. "Predict" or "forecast" means to assess the magnitude that a quantity will have at a specified time in the future. Forecasting may be achieved by any method known to those of ordinary skill in the art, including, but not limited to, any linear or non-linear method which processes the data in such a way that information is maintained and suitable predictions may be made as to the behavior of the data in future times. Forecasting methods include, but are not limited to, curve fitting and extrapolation, and combinations thereof.

"Curve fitting" means to calculate a curve that most closely approaches given data or a given data set. Suitable methods of curve fitting include, but are not limited to, using a function to fit the data, using a function based on known reaction kinetics of the reaction system used, using a power curve to fit the data, using a power curve with a time offset, filtering the data to eliminate noise or sampling effect, transforming the data (e.g. conversion to logarithms), using methods of least squares, associating each data point with a weight such that the significance of the point to the final fit is based on the data points' weight, calculating data points' weight based on the information contained within the data at the point the data was obtained, calculating weights based on historical data, selecting portions of the data stream, curve fitting values derived from the data (e.g. curve fitting the data's slope or second derivative), and combinations thereof.

"Extrapolation" means to estimate a function at a point which is larger or smaller than all the points at which the value of the function is known. Suitable methods of extrapolation include, but are not limited to, using parametric means wherein the analysis is based on a known function, using non-parametric means, deriving the value from regression of a limited data series, deriving the value the curvature or other dynamic behavior of a limited data series, deriving the value from any transform of the data, including all logical and mathematical transforms, and combinations thereof.

"Chromogenic onset time" is the time interval it takes for the optical absorption, or density, of a specified spectrum to change by a specified amount. "Chromogenic optical density" is the absorption of a specified spectrum after a fixed time. "Chromogenic optical density development rate" is the maximum change in absorption over time. "Turbidimetric onset time" is the time interval it takes for the amount of light scattering, or apparent optical density change due to the light scattering, of a specified spectrum to change by a specified amount. "Turbidimetric level" is the amount of light scattering, or apparent optical density change due to the light scattering, of a specified spectrum after a fixed time. "Turbidimetric development rate" is the maximum change in the amount of light scattering, or maximum apparent optical density change due to the light scattering, over time.

Predicting the results of a LAL and endotoxin reaction from data taken before the reaction is complete is based on its kinetic behavior. This in turn is based on its chemical pathway, a cascade of enzymes that are activated by the preceding step. The result is closely approximated by a power function, or power function with a delay. Such analysis may also be used to determine if the data stream is from a normal reaction or if something abnormal, such as bubble formation, is happening and the assay should be rejected.

LAL reagent is a mixture of zymogens, proteins which when activated become enzymes, associated factors, and inhibitors. Each lot is unique due to changes in the horseshoe crab population it's collected from, and differences in preparation. The major constituents are Factor C, which is activated by endotoxin and becomes an enzyme Activated Factor C, which in turn activates Factor B. Activated Factor B activates the Pre-Clotting Enzyme, which in turn either causes the clotting of coagulogen (for turbidimetric assays) or the development of color (for chromogenic assays).

The kinetics of enzyme cascades are discussed in "The Kinetics of Enzyme Cascade Systems," by Hemker and Hemker in The Procedures of the Royal Society, B (Biological Sciences), 173, 411-420 (1969). For open cascades, ones where the activated enzymes are stable, the simplest model is with product being formed as a power function of time.

$$[P]=at^b+[P_0]$$

where P is the cascade product (chromogenic indicator or clotted coagulogen); $P_0$ is the initial level; t the time of the reaction; and a and b are constants.

In practice, the reaction kinetics is more complex. The activation of Factor C can be from binding of endotoxin to multiple activation sites, where intermediate binding changes the structure and later bonding affinities. This allosteric modulation delays the activation of Factor C, which itself may be simply modeled as the replacement of endotoxin with Activated Factor C over a relatively short period of time. The entire process can be modeled as a delay roughly equivalent to the average time it took for this transfer to take place. There is no "amplification" of the endotoxin concentration from this first step, but the enzymes produced in later steps all increase rapidly as a chain reaction.

There are two pathways to LAL activation. One pathway is the endotoxin pathway and has three cascade steps. Thus, the reaction kinetics of the endotoxin pathway is approximately a third-order power function. The second pathway is the glucan pathway through Factor G. The glucan pathway has only one cascade step and the reaction kinetics is closer to a linear function. In many samples there will be no detectable glucan and the reaction kinetics will be that of the endotoxin pathway, or a higher-order power function. In more complex samples, both pathways can be activated with the kinetics becoming more complex. It is possible to separate the activity of both by their kinetic signatures, but the industry-accepted means of doing this is by chemically inhibiting one of the pathways.

It was surprisingly discovered, however, that monitoring both the endotoxin and glucan kinetic signatures can be used to determine what behaviors are "normal" and what could be caused by other factors, such as moving particles or growing bubbles in the optical path. This allows the user to validate the data or assess whether there is an anomaly in the sample analysis in addition to predicting the concentration of any endotoxin or glucan that may be present in the sample.

"Validate" as used herein means to substantiate, confirm the quality of, or establish the certainty of the analysis or progress of the analysis. When validating the suitability of the analysis and/or sample measurement, compendia methods may be used wherein at least two positive controls (samples spiked with LAL-reactive substances at the middle of the calibration range), three negative controls (blanks), and any other parameters specified by the manufacturer or compendia. The positive product control spikes must meet compendia requirements (between 50% and 200% spike yield), the negative control (difference between lowest level and blank, with the blank having a lower response level), and the manufacturers specification (e.g. the difference between a 0.005 EU/mL sample and blank, or onset time limits for certain standards). If these analyses are successful, they validate that the system and reagents are operating to specification and the sample measurement are "validated". To validate the data stream means that the data streams' behavior statistically corresponds to the expected behavior based on historical measurement data or the known reaction kinetics of the reaction between the detection reagent and LAL-reactive substance. This shows that the data stream is being generated by a change in the analysis chamber based on the LAL reaction and not a change in the chamber or optical path based on some abnormality, such as a bubble. Ultimately this differentiation would itself be validated by multiple tests on different reagents and lots and induced anomalies to confirm its operation, including, but not limited to, sample critical optical property blank reading, mixed sample/reagents/optional LAL-reactive substances, initial optical reading, smoothness of the change and rate of change of the critical optical property, closeness of fit to theoretical expected change, expectations on the noise level of the data, and the like. If test results appear incorrect the testing process may be stopped and an error message may be sent without producing an LAL-reactive substances measurement result. Likewise, if the test results appear as an output, the test results and or sample measurement is "validated".

It was also surprisingly discovered that some OD responses, such as absorbance over time, onset time, a maximum slope of absorbance over time, and absorbance after a fixed time, correlate well with endotoxin concentrations in a given sample. Accordingly methods are disclosed that are sensitive and fast, even at low endotoxin concentrations. The methods may be used with any photometric method, including turbidimetric and chromogenic methods.

In one embodiment, a method for measuring the concentration of a LAL-reactive substance in an aqueous sample is disclosed. The method may comprise contacting an aqueous sample with a detection reagent to form a prepared sample. A physical property of the prepared sample may be measured to obtain at least one sample measurement characteristic of the prepared sample. Curve fitting may then be used to forecast a concentration of the LAL-reactive substance the aqueous sample will have at a specified time in the future based on the sample measurement and a correlation developed between at least one standard measurement of a physical property of a solution with a known concentration of a LAL-reactive substance therein. The quality of the sample measurement may be validated using historical data and/or the standard measurement.

In another embodiment, the physical property may be an optical property. Suitable optical properties include, but are not limited to, transmittance, absorbance, turbidity, light scattering, optical density, color, color value, hue, spectrum, chemiluminescence, fluorescence, magnetic resonance of absorbance over time, time to a fixed change in absorbance, maximum slope of absorbance over time, and absorbance after a fixed time.

In yet another embodiment, the physical property may be a non-linear property such as reaction kinetics. The sample measurement quality may be validated using the non-linear property. Types of reaction kinetics include, but are not limited to, an endotoxin reaction, a glucan reaction, and a combination thereof. In another embodiment, the method may further comprise including at least one apparent time delay of the cascade initiation of the reaction as a variable in the curve fitting step.

In another embodiment of the invention, a method for measuring concentration of a LAL-reactive substance in an aqueous sample is disclosed comprising contacting the aqueous sample with a detection reagent to form a prepared sample. A physical property of the prepared sample may be measured to obtain at least two sample measurements characteristic of the prepared sample. A concentration of the LAL-reactive substance the aqueous sample will have at a specified time in the future may be forecasted. The forecasted concentration may be based on the sample measurements and a correlation developed between the non-linear behavior of at least three standard measurements of a physical property of a solution with a known concentration of a LAL-reactive substance therein.

In another embodiment, the physical property may be an optical property. Suitable optical properties include, but are not limited to, transmittance, absorbance, turbidity, light scattering, optical density, color, color value, hue, spectrum, chemiluminescence, fluorescence, magnetic resonance of absorbance over time, time to a fixed change in absorbance, maximum slope of absorbance over time, and absorbance after a fixed time.

In yet another embodiment, the physical property may be a non-linear property based on known reaction kinetics of the reaction between the detection reagent and LAL-reactive substance. Suitable reactions include, but are not limited to, an endotoxin reaction, a glucan reaction, and a combination thereof.

The invention is executable on a computer that includes a CPU, main storage, I/O resources and a user interface, such as a monitor, a manually operated keyboard, mouse, and printer. Optionally, the monitor may be a touch-screen. The computer may be a handheld device. Accordingly, systems for measuring the concentration of a LAL-reactive substance in an aqueous sample are also disclosed. The computer may be operatively connected to an optical reader. In an embodiment, the optical reader (not shown) includes fixed optical components. The fixed optical components may include low cost LEDs and photodiodes. The reader can include band-pass filters to increase the accuracy of optical measurements. The reader can also be modulated or electronically chopped to provide a reduction in optical noise, reject ambient light, and reject stray light. The reader may also include multi-plexed optical components such that the matrix of monitoring points can have a single component for each row or column and use a time-multiplexed reading scheme to lower component cost. Optical components such as windows, dark fields, apertures, lenses, reflectors, or diffusers can also be incorporated into the microfluidics cartridge itself to provide part of the optical path or increase the system's stability or sensitivity.

Suitable readers may use or perform a variety of optical sensing methods and measurements, including but not limited to, transmission, absorption, optical density, color, color value, hue, spectrum, turbidity, scattered light, chemiluminescence, and fluorescence.

The light sensed can be of a single wavelength, or spectral band, or multiple wavelengths or bands. Multiple light bands can be used to increase signal or reduce interference and noise. For example, monitoring at multiple frequencies for a change in optical density could reduce the interference of unstable sample color. The sensing method used may be capable of sensing changes in the fluid remotely, including more complex optical methods such as Raman spectroscopy, magnetic resonance, and surface plasmon resonance, and non-optical methods such as electrical capacitance, viscosity, magnetism, sonic resistance, and sonic refraction.

In another embodiment of the invention, a system for measuring a concentration of a LAL-reactive substance in an aqueous sample is disclosed. The system may comprise a memory and a processor operatively connected with the memory. The processor may be programmed to receive at least one input comprising a sample measurement. The sample measurement may be a measured physical property characteristic of the aqueous sample. The processor may also be programmed to use curve-fitting to generate at least one output. The output may comprise a forecasted concentration of the LAL-reactive substance the aqueous sample will have at a specified time in the future based on the sample measurement and a correlation. The correlation may be developed between at least one standard measurement of a physical property of a solution with a known concentration of a LAL-reactive substance therein. The outputs may also comprise validated sample measurements. The quality of the sample measurement may be validated using historical data and/or the standard measurement. The processor may also be programmed to report and/or store the output in the memory. The report may be a visual display on the monitor described above. The report may also be a print out from a printer as described above. In yet another embodiment, the system may further comprise an optical reader operatively connected to the processor. The optical reader may provide the inputs comprising at least one sample measurement and/or at least one standard measurement to the processor.

In another embodiment of the system the physical property may be an optical property. Suitable optical properties include, but are not limited to, transmittance, absorbance, turbidity, light scattering, optical density, color, color value, hue, spectrum, chemiluminescence, fluorescence, magnetic resonance of absorbance over time, time to a fixed change in absorbance, maximum slope of absorbance over time, and absorbance after a fixed time.

In yet another embodiment, the physical property may be a non-linear property, such as reaction kinetics. Suitable reactions include, but are not limited to, an endotoxin reaction, a glucan reaction, and a combination thereof. In another embodiment, the processor may be further programmed to include at least one apparent time delay of the cascade initiation of the reaction as a variable in the curve fitting step.

In another embodiment of the invention, a system for measuring a concentration of a LAL-reactive substance in an aqueous sample is disclosed. The system may comprise a memory; and a processor operatively connected with the memory. The processor may be programmed to receive at least one input. The input may comprise at least two sample measurements, wherein the sample measurements are a measured physical property characteristic of the aqueous sample. The processor may use a correlation developed between the non-linear behavior of at least three standard measurements of a physical property of a solution with a known concentration of a LAL-reactive substance therein to generate at least one output. The output may comprise a forecasted concentration of the LAL-reactive substance the aqueous sample may have at a specified time in the future. The processor may also be programmed to report and/or store the output in the memory. In yet another embodiment, the system may further comprise an optical reader operatively connected to the processor.

In another embodiment, the physical property may be an optical property. Suitable optical properties include, but are not limited to, transmittance, absorbance, turbidity, light scattering, optical density, color, color value, hue, spectrum, chemiluminescence, fluorescence, magnetic resonance of absorbance over time, time to a fixed change in absorbance, maximum slope of absorbance over time, and absorbance after a fixed time.

In yet another embodiment, the physical property may be a non-linear property. The non-linear property may be based on known reaction kinetics of the reaction between the detection reagent and LAL-reactive substance. Suitable reactions include, but are not limited to, an endotoxin reaction, a glucan reaction, and a combination thereof.

The methods disclosed herein use statistical correlations, open-ended methods that show a statistically-valid means of correlating measurements of samples with known concentrations of endotoxin, or factors derived from those measurements, to forecast endotoxin concentrations wherein the endotoxin concentration is unknown. Such measurements may include measurements such as onset time, maximum slope of absorbance over time, and absorbance after a fixed time. Additional measurements or factors may include, but are not limited to, time to optical density, time to filtered optical density (filter—using various methods to decrease the effect of variation or noise on the signal, in this case optical density over time, the simplest are averaging and methods of "data smoothing" (includes digital filters, segment regression, and rejecting outliers), slope of response, slope of filtered response, $2^{nd}$ derivative of response, $2^{nd}$ derivative of filtered response, higher order derivatives of response, higher order derivatives of filtered response, curvature (in its simplest form, the relationship of the various derivatives) of response, curvature of filtered response, factors from equations that are curve-fit to the response (e.g. with a simple regression, the intercept), factors from equations that are curve-fit to the filtered response, other data stream factors such as skew of derived values, integral sums, or vector products, factors from equations that are curve-fit to the response based on an assigned weight, and combinations thereof. As mentioned previously, the data set or each data point may be assigned a weight such that the significance of the point to the final fit is based on the data points' weight. The weight may be assigned based on factors including, but not limited to, significance, variation, information flow, and empirical testing.

In addition, the quality of the data may be evaluated by curve fitting to the response over time. Suitable curve fitting methods include the previously listed methods.

In another embodiment, a method for analyzing data from LAL-based assays in a predictive manner is disclosed. The prediction may include monitoring the dynamic linear slope of optical response against time. The linear slope may be measured over all the data points from the beginning of the assay to the current time. In another embodiment, the linear slope may be measured over a smaller number of consecutive data points prior to the current time. The number of consecutive data points chosen may vary based on the desired range of endotoxin detection. In another embodiment, at least three consecutive data points may be used to measure the slope. In yet another embodiment, the slope may be measured with more than three, but less than seven consecutive data points. Alternatively, the number of consecutive data points is greater than seven.

In yet another embodiment, the measured linear slope may be updated continuously for the latest collected set of three or more consecutive data points measured over time. The threshold value of the linear slope may be correlated with endotoxin levels. The threshold value of the linear slope may range from about 0.00001 to about 0.00005 optical density units per second.

Linear curve fitting or higher order curve fitting algorithms may be applied to the raw optical response data after the slope reaches a preset threshold value. Alternatively, the curve fitting algorithms may be applied to the raw response data after the raw response reaches a percentage of a specified onset value.

The predicted onset times for the threshold optical response may be redefined based on the geometry of the sample container. For example, the threshold OD value is set at 0.2 for kinetic chromogenic assay in a typical 96 well plate experiment. The OD value may be redefined appropriately for other geometries such as when a microfluidics cartridge is used.

The predicted onset times may be calculated using linear or higher order functions to fit the raw response data. In another embodiment, the predicted onset times may be updated continuously with time and reported according to appropriate criteria for convergence in prediction. In yet another embodiment, the predicted onset times are correlated with endotoxin levels and checked for linearity of response, as with measured onset times. In yet another embodiment, the predicted onset times are calculated for replicates of the same sample. The predicted onset times may also be calculated for replicates of positive spike recovery experiments from the same sample. In yet another embodiment, the predicted onset times are calculated for replicates of standards used for calibration. The predicted onset times may also be calculated for a control spike recovery experiment to validate the calculated calibration equation. In yet another embodiment, the dynamic linear slope calculations and the predicted onset time calculations are used to validate quality of optical response data being collected. For example, validating the quality of the optical response data may find anomalies in the data. Such anomalies may be caused by a variety of conditions, including but not limited to, discontinuities in optical response data due to air bubble formation in situ, misalignment of reaction wells with reader optical paths, or intermittent/systematic mechanical malfunctions in the sample reader.

EXAMPLES

Correlation Method

The following example describes the correlation method of the LAL measurement test. The LAL measurement test procedures and results of those test procedures are also described. The samples were prepared as in the kinetic chromogenic method. For this method, an aqueous endotoxin solution was prepared in various concentrations (0.005 Endotoxin Unit ("EU")/ml, 0.05 EU/ml, 0.5 EU/ml, and 5 EU/ml). Solutions without any endotoxins, or blanks, were also prepared and used as control solutions. The solutions were then incubated at 37° C. for 10 minutes. After incubation, each endotoxin concentration and a blank was dispensed (in triplicate) in a sample holder cleaned with NaOH and deoxycholate.

The optical density, or absorbance, of each sample was then measured at 405 nm using a spectrometer for over an hour. The onset time, or time each standard required to reach an absorbance of 0.2 was also measured. The measurements were recorded using a Perkin Elmer 1420 multi-label counter. Once all the measurements were collected and recorded, the samples' absorbance change with time were plotted.

The initial lag time and the initial slope of the OD response at the various concentrations were obtained from the plot and are shown in FIG. 1. These initial lag times and initial slopes may correlate well with endotoxin concentrations in a given sample. Accordingly, calibration curves may be generated using these initial lag times and initial slopes.

The calibration curves generated may be used to measure the concentration of the endotoxins in a sample of interest when the sample is treated in the same manner as the samples used to generate the calibration curves.

Forecasting and Validation

As discussed above, monitoring both the endotoxin and glucan kinetic signatures allows the user to validate or assess whether there is an anomaly in the sample analysis in addition to predicting the concentration of any endotoxin or glucan that may be present in the sample. The actual cascade reaction also has one or more factors inhibiting each of the enzymes. The endotoxin cascade is a 4-step cascade and the glucan cascade is a 2-step cascade. Both the endotoxin and glucan reactions, however, have inhibitory factors that affect their kinetics. In the horseshoe crab, these factors prevent clotting until a threshold is reached, which make them undesirable for analytical systems because the threshold limits the sensitivity. Part of the processing of the reagent is to remove these factors, which varies by manufacturer and lot. The effect on the kinetics is most-simply modeled as a fractional adjustment to the order of each reaction. In practice, the exact degree does not matter because various numerical techniques can be used that take advantage of the behaviors of power functions where reaction kinetics are the model.

These simplified models can be used to specify the function to be fit for early solutions of assays, to validate that data streams are being generated by LAL reactions and not some anomaly or error, and determine if responses are statistically similar. While models can always be made more representative of actual behavior by making them more complex, the advantages of a simpler model with a more-limited set of variables make these the ones preferred for such numerical analyses.

Example—Power Curve Function for Onset Time Forecasting

For either chromogenic or turbidimetric kinetic assays, the optical density is measured over time. The onset time, which is used as the metric for endotoxin level, is that time at which the LAL reaction has changed in optical density or absorption by a specified amount. Normally this time is calculated by interpolation between measurement points during which this level was exceeded. When the reaction has not yet reached its endpoint, but has shown enough change from its initial state to be distinguishable from the background noise, its results can be fit to a power function to forecast its future performance, including the onset time.

Forecasting future reaction performance may be done by taking a segment of data from a point at which the response is greater than the normal variance due to noise to its last recorded value and convert the change in optical response and time to logarithms. A power function is linear after a log-log conversion, so the best linear fit to these data can be used to fit them. Weights can be given to the fitting of these data based on several schemes, including their significance to the final result.

Figure 2:
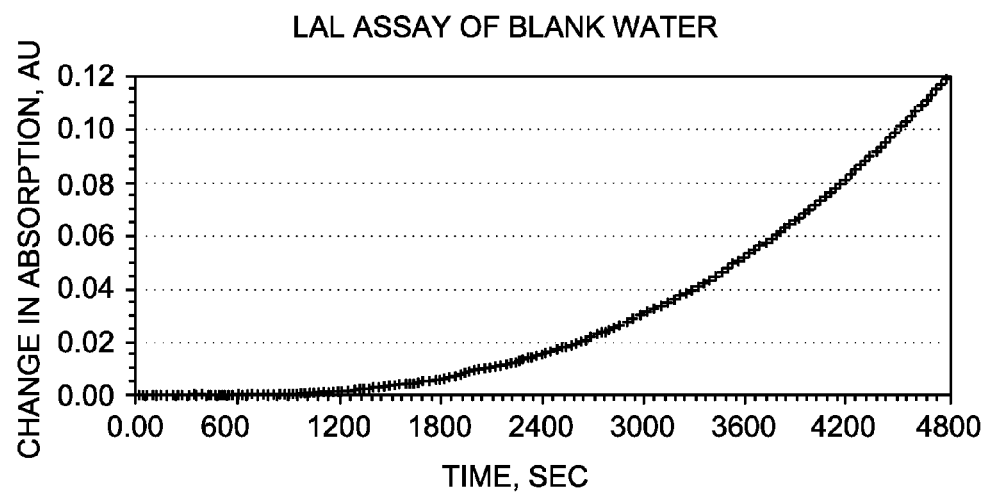
FIG. 2. is a chart of a data stream from a chromogenic kinetic LAL assay of blank water.

FIG. 2 is a chart of a data stream from a chromogenic kinetic LAL assay of blank water in a 10 uL cell with a 3.1 mm path length with absorption values measured every 30 seconds. The onset time used for the calibration and calculation of endotoxin levels was the time it takes for the change in optical density to reach 0.1 Absorption Units. This threshold is exceeded at about 4500 sec (75 min). Because the data is somewhat noisy different methods of interpolation give slightly different answers, with 4514 seconds being their average.

The forecast onset times may be forecast by fitting the last 20 data points (10 minutes of readings) to a power curve using a linear regression of the log values of both time and change in absorption and solving for the point the fit curve reaches the threshold value. The resulting forecast onset times are shown in FIG. 3.

Figure 3:
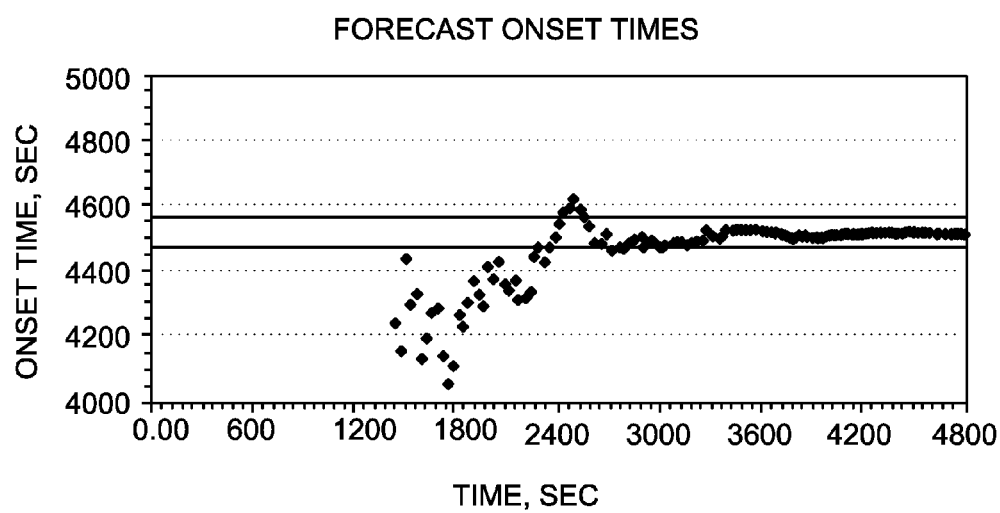
FIG. 3 shows forecast onset times of blank water.

The solid lines, also shown in FIG. 3, represent the 4514-second onset time threshold ±1.0% and form an error band. The forecast onset time (line with diamond symbols) is within the error band after 3000 seconds. Using a Pearson product-moment correlation coefficient ("Pearson's r") of greater than 0.999 for at least 2 consecutive readings, the forecast onset falls within the error band at 3300 seconds of analysis. Thus, the analysis time is reduced by over 1200 seconds, or 20 minutes. Moreover, the induced error is less than the normal variation of identical blank tests run in parallel (typically more than 2%), and a suitably precise answer for normal, or blank water analysis.

Example—Power Curve with Delay

A simple yet more accurate variation of using a power function for endpoint forecasting is to include the apparent time delay of the cascade initiation, due to the transfer of endotoxin levels to Factor C activity, and cascade step delays. Because every lot will be different, the use of a fixed time delay is less desirable than one that can vary.

This method involves fitting an equation where a time delay is an additional variable. This complicates the analysis substantially, resulting in equations that cannot be solved algebraically. A simpler method is to calculate discrete time delay offset data streams and determine which has the best fit using Pearson's r and the balance of residuals where they are most-evenly distributed across the range.

The same data set as above may be tested with time delays, or times subtracted from the actual time before log conversion, of 0, 30, 60, 90, 120, 150, 180, 210 and 240 seconds. After 1200 seconds of time, the best fits using both Pearson's r and residual balance are achieved with a 120 second delay-offset. The Pearson's r value criteria are met at 2610 seconds for an onset time value rounded to 4530 seconds. This is a 1920 second, or 32 minute reduction.

If 90 or 150 seconds of delay are used, results are a bit less accurate, but similar. For this reason it has been found that testing closely-spaced delay times is not necessary, and a rough interval, such as 30 seconds, is suitable. Finding the "best" delay time is less critical than getting a representative and stable fit which will effectively reduce noise while maintaining signal.

Example—Data Stream Validation

If a function describes a data stream well, newer points of data will cause the fit function to converge on a solution. If the solution does not converge, then the function does not describe the data well. This can be used as one of the simpler methods of checking a data stream for validity.

For example, if data where both the change in optical density and time have been converted to logs and fit to a simple power function, the difference between sequential solutions of the slope and intercept should get smaller over time. If slope and intercept solution do not get smaller (converge), then the data stream was corrupted by a non-cascade effects. Limits may be placed on the convergence from historical data, and if such limits are exceeded in a way that was statistically unlikely, the assay may be rejected for cause.

Figure 4:
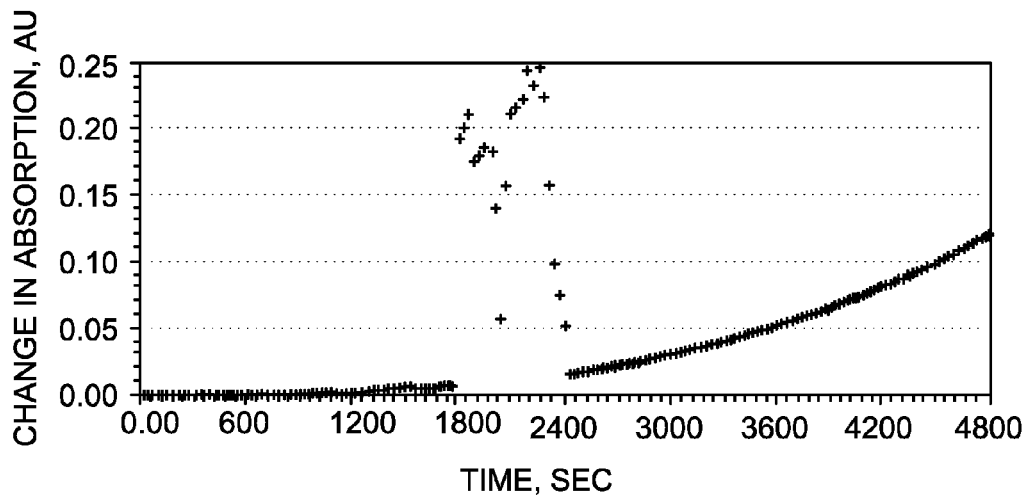
FIG. 4 shows a data stream with a disruption.
Figure 5:
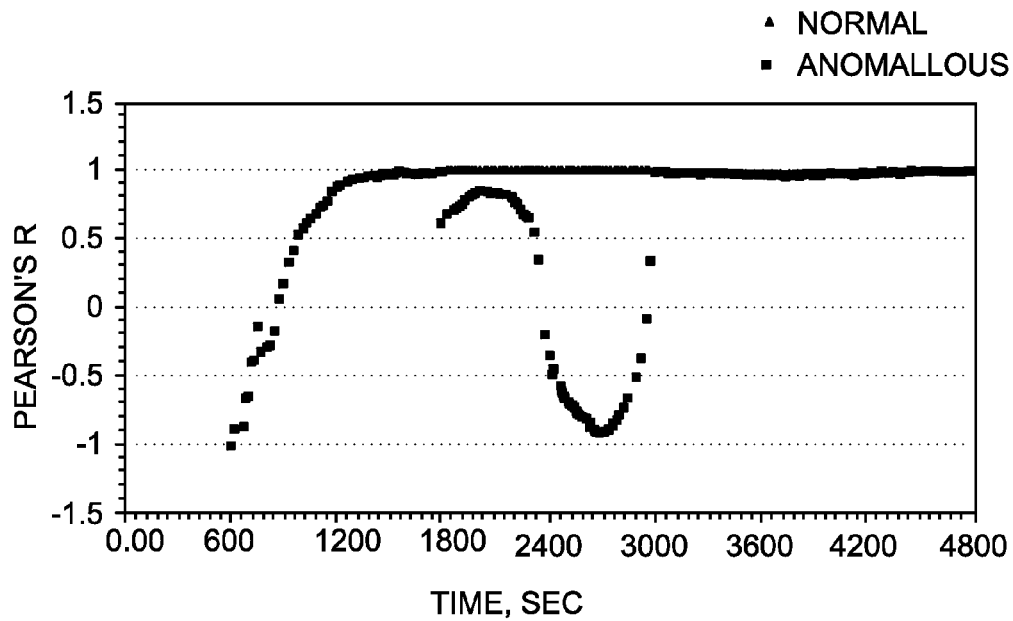
FIG. 5 shows the Pearson's r for normal and abnormal data streams.

To validate the data stream, an anomaly was added to the same data set as above. The anomaly was an actual optical anomaly from a different assay in a similar cell where a particle, bubble, or some other phenomenon disrupted the optical path. Without the disruption, the data stream's Pearson's r for a fit of 20 points (10 minutes) converges to 1.00 as time progresses. With the disruption, it starts to deviate immediately as shown in the data stream in FIG. 4. Thus a limit value of a Pearson's r of 1.00 may be set to discriminate between data that corresponds to the correct reaction kinetics, and those correspond to an anomaly. The may be seen in the "normal" and "abnormal" data streams as shown in FIG. 5.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A system for measuring a concentration of a LAL-reactive substance in an aqueous sample, said system comprising: (a) a memory; and (b) a processor operatively connected with said memory, where said processor is programmed to: (I) receive at least one input, said input comprising a sample measurement, wherein said sample measurement is a measured physical property characteristic of said aqueous sample; (II) use curve-fitting to generate at least one output, said output comprising: a forecasted concentration of said LAL-reactive substance said aqueous sample will have at a specified time in the future based on said sample measurement and a correlation developed between at least one standard measurement of a physical property of a solution with a known concentration of a LAL-reactive substance therein; and a validated sample measurement, wherein the quality of said sample measurement was validated using historical data and/or said standard measurement; and (III) report and/or store said output in said memory;
wherein said processor is further programmed to include at least one apparent time delay of a cascade initiation of a reaction as a variable in the curve-fitting step.

2. The system of claim 1, further comprising an optical reader operatively connected to said processor.

3. The system of claim 1, wherein said physical property is an optical property selected from the group consisting of transmittance, absorbance, turbidity, light scattering, optical density, color, color value, hue, spectrum, chemiluminescence, fluorescence, magnetic resonance of absorbance over time, time to a fixed change in absorbance, maximum slope of absorbance over time, and absorbance after a fixed time.

4. The system of claim 3, wherein said physical property is a non-linear property, said non-linear property selected from the group consisting of reaction kinetics of said reaction.

5. The system of claim 4, wherein said reaction is selected from the group consisting of an endotoxin reaction, a glucan reaction, and a combination thereof.

6. A system for measuring a concentration of a LAL-reactive substance in an aqueous sample, said system comprising: (a) a memory; and (b) a processor operatively connected with said memory, where said processor is programmed to: (I) receive at least one input, said input comprising a sample measurement, wherein said sample measurement is a measured physical property characteristic of said aqueous sample; (II) use curve-fitting to generate at least one output, said output comprising: a forecasted concentration of said LAL-reactive substance said aqueous sample will have at a specified time in the future based on said sample measurement and a correlation developed between at least one standard measurement of a physical property of a solution with a known concentration of a LAL-reactive substance therein; and a validated sample measurement, wherein the quality of said sample measurement was validated using historical data and/or said standard measurement; and (III) report and/or store said output in said memory;
wherein said processor is further programmed to include at least one apparent time delay of a cascade initiation of a reaction as a variable in the curve-fitting step to account for Factor C activity.

7. The system of claim 6, further comprising an optical reader operatively connected to said processor.

8. The system of claim 6, wherein said physical property is an optical property selected from the group consisting of transmittance, absorbance, turbidity, light scattering, optical density, color, color value, hue, spectrum, chemiluminescence, fluorescence, magnetic resonance of absorbance over time, time to a fixed change in absorbance, maximum slope of absorbance over time, and absorbance after a fixed time.

9. The system of claim 8, wherein said physical property is a non-linear property, said non-linear property selected from the group consisting of reaction kinetics of said reaction.

10. The system of claim 9, wherein said reaction is selected from the group consisting of an endotoxin reaction, a glucan reaction, and a combination thereof.

11. A system for measuring a concentration of a LAL-reactive substance in an aqueous sample, said system comprising: (a) a memory; and (b) a processor operatively connected with said memory, where said processor is programmed to: (I) receive at least one input, said input comprising a sample measurement, wherein said sample measurement is a measured physical property characteristic of said aqueous sample; (II) use curve-fitting to generate at least one output, said output comprising: a forecasted concentration of said LAL-reactive substance said aqueous sample will have at a specified time in the future based on said sample measurement and a correlation developed between at least one standard measurement of a physical property of a solution with a known concentration of a LAL-reactive substance therein; and a validated sample measurement, wherein the quality of said sample measurement was validated using historical data and/or said standard measurement; and (III) report and/or store said output in said memory;
wherein said processor is further programmed to include at least one apparent time delay of a cascade initiation of a reaction to account for Factor C activity.

12. The system of claim 11, further comprising an optical reader operatively connected to said processor.

13. The system of claim 11, wherein said physical property is an optical property selected from the group consisting of transmittance, absorbance, turbidity, light scattering, optical density, color, color value, hue, spectrum, chemiluminescence, fluorescence, magnetic resonance of absorbance over time, time to a fixed change in absorbance, maximum slope of absorbance over time, and absorbance after a fixed time.

14. The system of claim 13, wherein said physical property is a non-linear property, said non-linear property selected from the group consisting of reaction kinetics of said reaction.

15. The system of claim 14, wherein said reaction is selected from the group consisting of an endotoxin reaction, a glucan reaction, and a combination thereof.

16. The system of claim 15, wherein said at least one apparent time delay of a cascade initiation of said reaction is a variable in the curve-fitting step.

* * * * *